United States Patent [19]

Fedorov et al.

[11] Patent Number: 4,907,587
[45] Date of Patent: Mar. 13, 1990

[54] METHOD FOR SURGICAL CORRECTION OF MIXED AND HYPERMETROPIC ASTIGMATISM AND A DEVICE FOR CARRYING SAME INTO EFFECT

[76] Inventors: Svyatoslav N. Fedorov, ulitsa Dostoevskogo, 21, kv. 32; Albina I. Ivashina, utlitsa 800-letia Moskvy, 8, kv. 73; Valery B. Gudechko, ulitsa Ostrovityanova, 51, kv. 72; Olga G. Alexandrova, ulitsa 8l2 goda, I, kv. 139; Nadezhda K. Korshunova, 3 Mikhailovsky pereulok, 8, korpus 2, kv. 4, all of Moscow, U.S.S.R.

[21] Appl. No.: 256,503

[22] Filed: Oct. 12, 1988

[51] Int. Cl.$^4$ .............................................. A61B 19/00
[52] U.S. Cl. ...................................... 606/28; 128/399; 128/847
[58] Field of Search ................ 128/303.1, 303 R, 305, 128/399, 897, 303.11–303.14; 101/40 S

[56] References Cited

U.S. PATENT DOCUMENTS

| 2,108,934 | 2/1938 | Albright | 128/399 |
| 3,900,018 | 8/1975 | Painno | 128/847 |
| 4,183,353 | 1/1980 | Gallub | 101/405 |
| 4,326,529 | 4/1982 | Doss et al. | 128/303.1 |
| 4,381,007 | 4/1983 | Doss | 128/303.1 |
| 4,712,543 | 12/1987 | Baron | 128/303.1 |

FOREIGN PATENT DOCUMENTS 831119  5/1981  U.S.S.R. .......................... 128/303.1

*Primary Examiner*—Lee S. Cohen
*Assistant Examiner*—David Shay
*Attorney, Agent, or Firm*—Burgess, Ryan & Wayne

[57] ABSTRACT

The surgical correction is carried out with the aid of thermocoagulation of the cornea along the lines appropriately oriented with respect to the minimum refractive power meridian and to the distal points of the eyeball central optic zone. Two of such lines are essentially circular arcs, while two other lines are the sides of two angles the bisector of which is the minimum refractive power meridian. Provision is also made for a device for preliminary marking out of the eyeball, aimed at carrying out thermocoagulation along said lines. The device is in fact a cylinder-shaped housing which accommodates special elements adapted to be brought in contact with the corneal surface upon placing the housing on said surface in order to obtain the impressions of the lines along which thermocoagulation is then carried out.

8 Claims, 1 Drawing Sheet

METHOD FOR SURGICAL CORRECTION OF MIXED AND HYPERMETROPIC ASTIGMATISM AND A DEVICE FOR CARRYING SAME INTO EFFECT

FIELD OF THE INVENTION

The present invention relates generally to medicine, more specifically to ophthalmology and is particularly concerned with a method for surgical correction of mixed and hypermetropic astigmatism, as well as with a device for marking out the eyeball when carrying said method into effect.

BACKGROUND OF THE INVENTION

Mixed and hypermetropic astigmatism proves to be the most commonly encountered eye disease in humans, which has both natural and post-operative origin. A number of surgical techniques have been suggested up till now for treatment of mixed and hypermetropic astigmatism of which the so-called thermocoagulation methods have gained the most extensive application. The essence of such methods resides in that some cornea areas are exposed to the effect of elevated temperature with the aid of a needle penetrating into the cornea by 40 to 50 μm, the temperature at the needle point being within 100° and 200° C. As a result of such a thermal effect there occurs structural alteration of the cornea and hence redistribution of stresses therein, which should result, with appropriately selected thermocoagulation zones, in elimination of mixed and hypermetropic astigmatism in patients operated upon.

Thus, for instance, one prior-art method for surgical correction of astigmatism is known to provide local thermocoagulation (cf.. e.g., V. B. Gudechkov, the paper "Keratocoagulation in surgical correction of astigmatism" in: Collected proceedings of the Moscow research institute for microsurgery of the eye, Moscow, 1981, pp. 78–83 (in Russian). When carrying said method into effect first one should find, using any known technique, the position of an optically weak meridian known as the meridian of the minimum refractive power. Then point coagulation is carried out on the diametrally opposite, with respect to the central optical zone, sides on the area of the optically weak meridian, the coagulation points being spaced along a circumference having, as a rule, a diameter of 6 mm. However, the aforesaid method suffers from a number of substantial disadvantages concerned with the onset of nonuniform zonal corneal stresses and hence post-operative complications in the course of cicatrization. In particular, the method is fraught with the formation of stresses in the optically weak meridian and may also lead to corneal deformation, which to a considerable extent affects the efficacy of such a surgery and is frequently accompanied by relapses of astigmatism.

Another prior-art method for surgical correction of hypermetropic astigmatism, according to S. N. Fyodorov and V. B. Gudechkov (SU, A, 1,090,385) is known to provide preliminary marking-out of the cornea, wherein the optic centre of the eyeball and the central optic zone are first found out, followed by radial marking-out of the cornea from the optic zone towards the corneal periphery along four meridians. Marking-out over, point coagulation is carried out along said radial directions, using a needle heated up to 100° or 200° C. and applied for 0.3 to 0.5 sec. As practical experience shows such a radial arrangement of the coagulation points results, however, in inadequate corneal deformation, which is accompanied, on the one hand, by higher refraction in all the four meridians, and on the other hand, leads to relapses of astigmatism.

SUMMARY OF THE INVENTION

It is an object of the present invention to select such an arrangement of coagulation points, in a method for surgical correction of mixed and hypermetropic astigmatism, as to provide favourable cicatrisation conditions and preclude a possibility of corneal deformation.

It is another object of the present invention to provide a method for surgical treatment of mixed and hypermetropic astigmatism which will be capable of drastically reducing relapses of astigmatism or will practically eliminate such relapses.

It is one more object of the present invention to provide a device for marking out the eyeball cornea by making impressions thereon, which will make it possible to carry out thermocoagulation at a high degree of accuracy of arrangement of the coagulation points.

It is also an object of the invention to simplify surgeon's work in the course of surgery and to cut down the operating time.

The aforesaid and further objects are accomplished due to the fact that in surgical correction of mixed and hypermetropic astigmatism one should first determine the position of the minimum refractive power meridian, using any heretofore-known method suitable for the purpose. Then thermocoagulation is carried out along two arcs of circles having the same radius of curvature, tangent to the distal points of the patient's eyeball central optic zone, which lie on said minimum refractive power meridian and are arranged symmetrically with respect to an axis perpendicular to said meridian and passing through the optic eyeball centre. Such thermocoagulation is performed first on one arc, then on the other. Next the thermocoagulation is carried out on the sides of two angles, the vertex of each of said angles being one of said distal points, while the minimum refractive power meridian serves as the bisector of said angles. The sides of each of said angles diverge in the direction away from the eyeball optic zone, and coagulation is first made on the sides of one of the angles, then on the sides of the other.

Such a method for surgical correction of mixed and hypermetropic astigmatism ensures uniform corneal stresses both radially, due to thermocoagulation on the sides of said angles, and angularly under the action of thermocoagulation along the circular arcs. Besides, tissue ∓swelling" and corneal deformation are practically ruled out, whereby corneal refraction remains unaffected and any relapses of astigmatism are eliminated completely.

The herein-proposed surgery is expedient to carry out after preliminary marking-out of the cornea, for which purpose there are formed thereon the impressions of circular arcs and angle sides appropriately oriented with respect to the minimum refractive power meridian and to the distal points of the eyeball central optic zone. Then coagulation is carried out following said impressions. Such a preliminary marking-out makes it possible to perform coagulation exactly along the preassigned lines, which adds still more to the efficacy of the surgery and speeds up the latter. Besides, the preliminarily made marking-out cuts down abruptly the time spent for thermocoagulation proper.

The present invention also makes provision for a special device for marking out patient's eyeball when carrying out correction of mixed and hypermetropic astigmatism. The device comprises a hollow cylinder-shaped housing the diameter of whose inner surface is equal to the corneal diameter. The housing accommodates two arcuate elements of the same radius of curvature, said elements being connected, through their ends, to the inner surface of the housing so that each of the arcuate elements subtends a chord having a length equal to 0.6 or 0.7 the diameter of the housing inner surface. The apices of the arcuate elements lie in the same diametrical plane and are symmetrical with respect to the longitudinal plane of the housing that is square with the plane wherein the apices of the arcuate elements are arranged. The arcuate elements are so arranged in the housing that, when the housing is put onto the cornea, the edges of the elements should leave an imprint on the iris to facilitate subsequent coagulation. The housing accommodates also two pairs of rectilinear elements which are divergent in each of said pair from the arc apex to the inner surface of the housing to establish an angle the bisector of which is in fact the diametrical plane passing through the apices of the arcuate elements. Said rectilinear elements are adapted to interact with iridal surface when the end of the housing is put onto said surface for making impressions according to which subsequent coagulation is carried out.

Such a comparatively simple construction of the device for marking out the eyeball cornea provides for convenience for surgeon's work, simplifies subsequent coagulation and ensures high degree of accuracy of coagulant's formation. This in turn ensures the required stress distribution over the cornea and hence substantially rules out any relapses of astigmatism.

It is expedient, in view of producing clear-cut impressions when marking out the corneal surface, that the edges of the arcuate and rectilinear elements be sharp and vertically curved, the radius of their curvature being equal to the radius of corneal curvature.

An additional convenience is provided for an operating surgeon due to the provision of a radial rod arranged in the housing longitudinal plane passing along the bisector of an angle established by the rectilinear elements and serving as a sight for orientation along the minimum refractive power meridian.

BRIEF DESCRIPTION OF THE DRAWINGS

In what follows the present invention is illustrated by a detailed description of a specific embodiment thereof but not bounding the present invention, with reference to the accompanying drawings, wherein.

BEST MODE OF CARRYING OUT THE INVENTION

The herein-proposed method resides in applying point thermocoagulation along the lines apropriately oriented with respect to the eyeball meridian possessing the minimum refractive power and the eyeball central optic zone. To this end, first one has to determine the position of the minimum refractive power meridian and the position of the distal points of the central optic zone lying on said meridian, by virtue of ophthalmometry, refractometry and visiometry. Next thermocoagulation is carried out with the aid of a needle heated up to 100° or 200° C., with which the cornea is punctured for a depth of 5 or 6 $\mu$m at 0.5 mm intervals. One row of the thus-made punctures is arranged along an arc which passes with its apex through the distal point of the central optic zone, which lies on the minimum refractive power meridian, while another row of the punctures is arranged along the other arc passing through a diametrically opposite distal point of the central optic zone. Both of said arcs have the same radius of curvature and are arranged symmetrically with respect to plane which is square with said meridian and passes through the centre of the optic zone, while each of such arcs subtends a chord having a length equal to 0.6 or 0.7 the diameter of the cornea. Coagulation is so carried out as to establish first one of the arcs, then the other. Then coagulation is carried out along the straight lines emerging in pairs from the apex of each arc towards the corneal periphery, said lines being in fact the sides of two angles, while said meridian serves as the bisector for each of said angles. In this case coagulation is performed first on the sides of one angle, then on those of the other. The surgery over, a solution of an antibiotic is injected under the conjunctiva and a gauze bandage is applied.

Such a surgery can be carried out, as a matter of fact, under a microscope without any auxiliary appliance, which however involves some difficulties as for an exact mutual arrangement of the coagulation points and orientation of the coagulation lines with respect to said meridian. Meanwhile, it is the arrangement of the coagulation points with respect to the central optic zone and to the minimum refractive power meridian that proves to be the most important factor of the whole surgery involved. That is why the present invention makes provision also for a device for marking out the eyeball cornea when correcting mixed and hypermetropic astigmatism, which makes it possible to obtain, before the surgery, an impression of lines on the corneal surface along which the thermocoagulation points should be arranged in the course of surgery.

Figure 1:
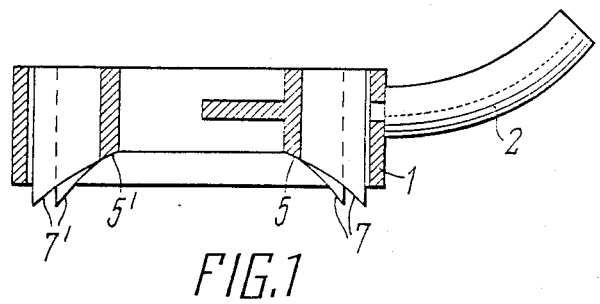
FIG. 1 is a schematic longitudinal sectional view of a device for marking out the eyeball cornea for subsequent surgical treatment with the use of thermocoagulation, according to the invention.
Figure 2:
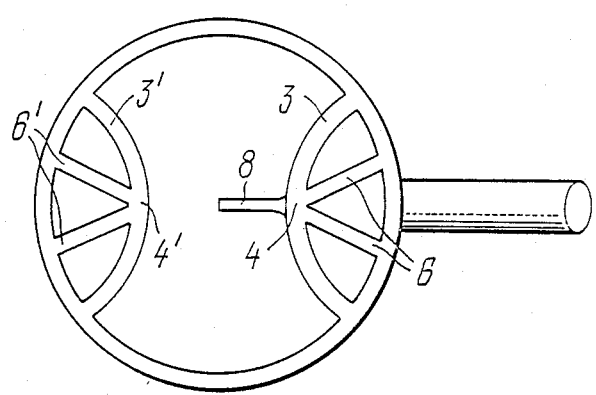
FIG. 2 is a plan view of the device of FIG. 1.

As can be seen from FIGS. 1 and 2, the proposed device for marking out the cornea in astigmatism correction comprises a hollow cylinder-shaped housing 1 with a handle 2 for holding the device by the operating surgeon and manipulating said device during surgery. The housing is made of a material inert to the ocular fluid medium, e.g., stainless steel. The inside diameter of the cylinder-shaped housing is selected to be equal to the diameter of the eyeball cornea. The housing accommodates similar arcuate elements 3 and 3' also made of a material inert to the eye humor and secured, with their ends, on the inner surface of the housing 1. Both of the arcuate elements 3 and 3' have the same radius of curvature and subtend a chord having a length equal to 0.6 or 0.7 the diameter of the inner surface of the housing 1. Apices 4 and 4' of the respective arcuate elements 3 and 3' lie in the same diametral plane symmetrically with respect to the central longitudinal plane which is square with the plane passing through the apices 4 and 4', while edges 5 and 5' of the respective arcuate elements 3 and 3' are slightly sharpened so as to leave a finer impression on the corneal surface but shall by no means be too sharp for the cornea not to be damaged. Provision may also be made for the use of a serrated edge, the spacing between the serrations being the same as that between the thermocoagulation points. The edges 5 and 5' of the respective arcuate elements 3 and 3' are so arranged with respect to the ends of the housing 1 that, when the housing is put onto the corneal surface, said edges contact the cornea to leave an impression thereon either as indented areas or (whenever use is made of an appropriate pigment which is then washed out by the ocular fluid) as a pigmented line.

Besides, the device for marking out the cornea incorporates two pairs of rectilinear elements 6 and 6' of which two elements 6 run from the apex 4 to the inner surface of the housing 1 and are secured on said surface to establish an angle confined between them, the bisector of said angle being a diametral plane passing through the apices 4 and 4' of the arcuate elements. Two other elements 6' pass from the apex 4' to the inner surface of the housing 1 to define an angle therebetween, the bisector of said angle being the same diametral plane passing through the apices 4 and 4'. Edges 7 and 7' of the rectilinear elements 6 and 6', as it can readily be seen from FIG. 1, are curved to a degree of curvature equal to that of the cornea so as to provide an intimate contact therewith during the marking-out. As in the case of the arcuate elements the edges 7 and 7' may be either slightly sharpened or serrated and should satisfy the same requirements as imposed upon the edges 5 and 5'.

The device as shown in FIGS. 1 and 2 is also provided with a sight 8 aimed at orienting the device with respect to a selected meridian and made as a slender rod arranged radially in the longitudinal plane of the housing which passes through the bisector of the angle established by the rectilinear elements.

Since every patient has his/her individual corneal parameters, i.e., degree of curvature and diameter, as well as dimensions of the central optic zone, it is expedient that a set of the aforesaid devices for marking out the eyeball cornea should be provided, incorporating such devices differing in the inside diameter, spacing between the arcuate elements, chords subtended by said elements, radius of curvature of the edges, and so on, in order to take account of the whole diversity of dimensional characteristics of human cornea within reasonable limits of the working parameters of the proposed device.

Use of the aforedescribed device for marking out the eyeball cornea during correction of astigmatism does not change the surgery as such, since thermocoagulation is likewise effected by a preheated needle which is to penetrate into the cornea under the above-specified conditions, the sole exception being that the surgeon is to perform the following manipulations before proceeding to thermocoagulation. Once local anesthesia has been given the surgeon places the movable portion of a surgical microscope above the patient's head in such a manner that an imaginary line that interconnects the centres of the microscope eyepieces should be parallel to another imaginary line that interconnects the canthi. Then the patient is to look through the respective eyepiece of the microscope with his/her eye to be operated upon, while the surgeon marks, using the blunt blade edge, the minimum refractive power meridian on the corneal surface against the degree-graduated scale of the microscope eyepiece in keeping with the ophthalmometry findings. Next the surgeon takes the device for marking out the eyeball cornea which has been preselected in accordance with the corneal dimensions, the radius of its curvature and the size of the central optic zone and applies the device so that the sight 8 should align with the minimum refractive power meridian marked out on the corneal surface, whereupon the device is tightly pressed against the cornea. After the device is removed from the cornea impressions of the arcuate and rectilinear elements are left on the corneal surface, against which thermocoagulation is then carried out.

A number of surgeries have been carried out with the use of the proposed device for marking out the cornea, the case histories of some of them being cited hereinbelow.

EXAMPLE 1

Male patient S., 50. Diagnosis—OD—aphakia, high-degree mixed astigmatism. OS—emmetropia.
Ophthalmometry findings—98°-37.5$^D$; 12°-42.5$^D$
Visual acuity—OD=0.125 cyl.+4.0$^D$ ax. 10°=1.0
Clinical refraction M—0.5$^D$.

The patient was subjected to surgery as described hereinbefore with the preliminarily marked out cornea. Spacing between the thermocoagulation points, 0.5 mm; the chord length, 0.6 the corneal diameter.

An immediate effect of surgery as per the ophthalmometry findings—92°-52.2$^D$, 2°-42.25$^D$.

Examination findings after a four-month follow-up period:
Ophthalmometry—96°-41.75$^D$; 0°-41.75$^D$
Clinical refraction—emmetropia.
Visual acuity—OD=0.6 cyl.+1.0$^D$ ax. 95°—1.0
No changes in the examination findings upon one-year follow-up period occurred.

Thus, the herein-proposed method was successful in a complete correction of the 5.0$^D$ corneal astigmatism, thus increasing the visual acuity from 0.125 to 0.6 without correction.

EXAMPLE 2

Female patient K, 29. Diagnosis—OD—high-degree mixed astigmatism, amblyopia, OS—medium-degree myopia.
Examination findings:
Ophthalmometry—92°-47.0$^D$; 0°-43.5$^D$
Clinical refraction—myopia-1.75$^D$
Visual acuity—OD=0.2 cyl.+3.5$^D$ ax. 90°=0.6

The patient was subjected to surgery as described hereinbefore using the device for marking out the cornea. Spacing between the thermocoagulation points, 0.5 mm; the length of the arc-subtended chord, 0.65 the average corneal diameter.

An immediate effect of surgery as per the opthalmometry findings—4°-54.0$^D$, 96°-42.0$^D$.

Examination findings after a five-month follow-up period:
Ophthalmometry—98°-47.25$^D$; 8°-47.25$^D$
Visual acuity—OD=0.6 (not amenable to correction).

Examination findings upon a seven-month follow-up period:
Ophthalmometry—50°-46.6$^D$ 144°-46.1$^D$
Visual acuity—0.8 (not amenable to correction).

Thus, the herein-proposed method make it possible to fully correct the 3.5$^D$ astigmatism and to increase the visual acuity from 0.2 to 0.8 without correction.

EXAMPLE 3

Female patient L., 44. Diagnosis—OD—compound hypermetropic astigmatism, amblyopia.
Examination findings:
Ophthalmometry—29°-41.5$^D$; 115°-45.25$^D$
Clinical refraction-hypermetropia+1.0$^D$ Visual acuity—OD=0.25 sph.+0.5$^D$ cyl.+3.5$^D$ ax. 105°=0.6

The patient was subjected to surgery as described hereinbefore with the use of the device for marking out the cornea. The length of the arc-subtended chord, 0.75 the corneal diameter.

An immediate effect of surgery as per the opthalmometry findings—38°-54.0$^D$, 122°-42.3$^D$.

Examination findings after a five-month follow-up period:
- Opthalmometry—20°-43.95$^D$; 102°-44.75$^D$
- Clinical refraction—hypermetropia+1.5$^D$
- Visual acuity—OD=0.8 sph.+1.0=1.0

Thus, the herein-proposed method made it possible to correct the 3.75$^D$ corneal astigmatism, which increased the visual acuity from 0.25 to 0.8 without correction.

The exemplary clinical cases cited hereinabove demonstrate that the proposed method is instrumental in attaining good results in cases of mixed and hypermetropic astigmatism and yields practically no relapses of the disease.

Given hereinabove have been specific examples of practical realization of the method for treatment of mixed and hypermetropic astigmatism and of the device for marking out the eyeball cornea for facilitating such a surgery. It is readily understood that a great deal of changes and modifications may be introduced into the present invention by those skilled in the art, provided such changes and modifications do not escape beyond the spirit and scope of the present invention as defined by the claims that follow.

What we claim is:

1. A method for surgical correction of mixed and hypermetropic astigmatism, comprising:
   (a) determining the position of the minimum refractive power meridian;
   (b) carrying out thermocoagulation of two arcs having chords and circumferences of the same radius of curvature tangent to the distal points of the patient's eyeball central optic zone, which points lie on said minimum refractive power meridian and are arranged symmetrically with respect to an axis perpendicular to said meridian and passing through the optic center of the patient's eyeball, said thermocoagulation being performed first on said one of said two arcs, then on said other of said two arcs; and
   (c) carrying out thermocoagulation on both sides of two angles, the vertex of each of said angles being one of said distal points, while said minimum refractive power meridian serves as the bisector of said angles, the sides of each of said angles diverging in a direction away from the eyeball optic zone, and coagulation is first performed on the sides of one of said angles, then on the sides of the other of said angles.

2. A method as claimed in claim 1, wherein the eyeball cornea is preliminarily marked out to form the impressions of arcs and angles on the corneal surface, said impressions being appropriately oriented with respect to the minimum refractive power meridian in such a manner that the arcs pass through the distal points of the patient's eyeball central optic zone, while the sides of the angles converge at said distal points.

3. A method as claimed in claim 1, wherein the length of the chord of each of the arcs equals 0.6 to 0.7 the average corneal diameter.

4. A device for marking out the eyeball cornea during correction of mixed and hypermetropic astigmatism, comprising a hollow cylinder-shaped housing the diameter of whose inner surface is equal to the corneal diameter, the housing having an end which engages the eye, and two arcuate elements having the same radius of curvature and secured with their ends on the inner surface of the housing, each of the arcuate elements subtending a chord having a length equal to 0.6 to 0.7 the housing inner surface diameter, while the apices of the arcuate elements lie in the same diametral plane and are symmetrical with respect to the housing longitudinal plane which is aligned with a diametral plane passing through the apices of the arcuate elements; said arcuate elements form arcs and are so arranged with respect to the housing as to interact with the cornea when the housing is placed on the corneal surface; two pairs of rectilinear elements which are arranged, in each pair, from said arc to said inner surface at an angle to each other, the bisector of said angle being a diametral plane passing through the apices of the arcs, while said rectilinear elements are so arranged with respect to the housing that when the latter is placed on the corneal surface, said rectilinear elements get in contact with said surface, with the result that impressions are left on the corneal surface of both the arcs and the angle sides, according to which impressions coagulation is then carried out.

5. A device as claimed in claim 4, having a radial rod arranged in the longitudinal plane of the housing which passes through the bisector of the angle established by the rectilinear elements, said rod serving as the sight for orienting the device with respect to the minimum refractive power meridian.

6. A device as claimed in claim 4, wherein the arcuate and rectilinear elements have edges which are sharpened on the end placed on the corneal surface, said edges being curvilinear in the longitudinal plane of the housing and having the radius of curvature equal to that of the corneal surface.

7. A device as claimed in claim 6, wherein the edges of said arcuate and rectilinear elements are made serrated, the spacing between serrations corresponding to a required spacing between the thermocoagulation points.

8. A kit for marking out the eyeball in correction of mixed and hypermetropic astigmatism, comprising a plurality of the devices for marking out of the eyeball as claimed in claim 4, featuring different distance between the arc apices and different diameter of the inner surface of the housing.

* * * * *